United States Patent [19]

Hayashi et al.

[11] Patent Number: 6,121,057
[45] Date of Patent: Sep. 19, 2000

[54] METHODS OF DETECTING ANTIBODIES TO α-FODRIN AND FRAGMENTS THEREOF IN DIAGNOSING SJÖGRENS'

[75] Inventors: Yoshio Hayashi, 1-8-301, Jounancho 2-chome, Tokushima 770; Hiromu Sugino, Tokushima, both of Japan

[73] Assignees: Takeda Chemical Industries, Ltd., Osaka; Yoshio Hayashi, Tokushima, both of Japan

[21] Appl. No.: 09/076,938

[22] Filed: May 13, 1998

Related U.S. Application Data

[62] Division of application No. 08/736,434, Oct. 24, 1996, abandoned.

[30] Foreign Application Priority Data

Apr. 23, 1996 [JP] Japan ..................... 8-100765

[51] Int. Cl.⁷ ............................................... G01N 33/536
[52] U.S. Cl. ........................... 436/536; 435/7.8; 435/194; 530/350
[58] Field of Search ................ 435/7.8, 7.1, 15; 436/501; 530/350, 352, 412, 395, 415, 416, 418, 427, 835, 324, 325, 326

[56] References Cited

U.S. PATENT DOCUMENTS

| | | | |
|---|---|---|---|
| 5,118,606 | 6/1992 | Lynch et al. | 435/7.1 |
| 5,182,262 | 1/1993 | Leto | 514/13 |
| 5,610,008 | 3/1997 | Schnitzer et al. | 435/4 |
| 5,661,150 | 8/1997 | Shirasaki et al. | 514/252 |
| 5,837,706 | 11/1998 | Shirasaki et al. | 514/252 |

FOREIGN PATENT DOCUMENTS

WO 92/01935   2/1992   WIPO.

OTHER PUBLICATIONS

Haneji et al, Science, Apr. 25, 1997, vol. 276(5312), pp. 604–607 (abstract).
Heltianu et al, Circ. Res., Apr. 1986, vol. 58(4), pp. 605–610.
Hentati, B et al, Journal Autoimmunity, Apr. 1991, vol. 4(2), pp. 341–356.
Narvanen, O. et al, Nov. 1987, vol. 224, No. 1, pp. 156–160.
Shile, P et al, Experimental Biology, Fed. Proc. vol. 44(3), 1985, p. 742, abstract #1935.
Martin, SJ et al. Journal of Biological Chemistry, Mar. 24, vol. 270(12), pp. 6425–6428, 1995.
Chan, et al., J. of Clin. Invest., 87:68–76 (1991).
R. Moon, et al., J. of Bio. Chem., 265:4427–4433 (1990).
Chan, et al., Nucleic Acid Research, 17:2233–2244, 1990.

*Primary Examiner*—Christopher L. Chin
*Assistant Examiner*—Ginny Allen Portner
*Attorney, Agent, or Firm*—David G. Conlin; Cara Z. Lowen; Dike, Bronstein, Roberts & Cushman, LLP

[57] ABSTRACT

Screening of the autoantibodies and autoantigens which are specific to Sjögren's syndrome, particularly primary Sjögren's syndrome, and provision of a prophylactic and therapeutic drug for Sjögren's syndrome, particularly primary Sjögren's syndrome, and a highly sensitive diagnostic agent for Sjögren's syndrome. The α-fodrin or α-fodrin fragment of the invention is an antigen to the autoantibodies specifically found in Sjögren's syndrome and this autoantigen finds application as a prophylactic and therapeutic drug for autoimmune diseases, particularly Sjögren's syndrome, or a diagnostic agent for such diseases.

4 Claims, 4 Drawing Sheets

METHODS OF DETECTING ANTIBODIES TO α-FODRIN AND FRAGMENTS THEREOF IN DIAGNOSING SJÖGRENS'

This Application is a Divisional of application Ser. No. 08/736,443 filed Oct. 24, 1996, now abandoned.

TECHNICAL FIELD

The present invention relates to new uses for α-fodrin and α-fodrin fragment proteins.

BACKGROUND ART

Sjögren's syndrome is said to be an autoimmune disease whose cardinal manifestation is a sicca syndrome associated with keratoconjunctivitis sicca and chronic sialadenitis but the mechanisms of its onset remain to be elucidated.

Diagnosed as Sjögren's syndrome is either a glandular (primary) syndrome which is confined to the lacrimal and salivary glands and clinically characterized by the so-called dry eye/dry mouth symptom or an extraglandular (secondary) syndrome characterized by a broad spectrum of generalized symptoms involving the liver, lung, thyroid gland, pancreas, kidney, and other organs. It is also known that the glandular syndrome progresses to the extraglandular syndrome in many cases and, though rarely, gives rise to malignant lymphoma.

As autoantibodies detected in Sjögren's syndrome, SS-A/Ro and SS-B/La are known. The corresponding antigens of these antibodies have already been identified but their specificity is low, with patients possessing autoantibodies to these antigens accounting for 40–60% of the total population of patients with Sjögren's syndrome. Moreover, in many cases SS-A/Ro- or SS-B/La-positive patients have complications such as systemic lupus erythematosus and rheumatism [Journal of Clinical Investigation, 87, p68–76, 1991; and Nucleic Acids Research, 17, p2233–2244, 1989].

In view of the above findings, those antibodies or antigens are regarded as indicators of all autoimmune diseases inclusive of Sjögren's syndrome. However, neither a specific autoantigen nor a specific autoantibody that could be a specific indicator of primary Sjögren's syndrome is not heretofore known.

α-Fodrin is one of subunits of fodrin which is a macromolecular actin-binding protein present immediately beneath the plasma membrane of cells. Fodrin forms high-order structures such as the fodrin network and is considered to be associated with the morphogenesis of cells and the migration of secretory granules to the surface membrane.

It has recently been reported that in programmed cell deaths such as apoptosis, the full-length α-fodrin of 240 K is restrictively cleaved by proteases to yield α-fodrin protein fragments [Journal of Biological Chemistry, 270, p6425–6428, 1995]. Moreover, as the proteases causing such restricted cleavage of α-fodrin, trypsin, chymotrypsin, and calpain are known [Journal of Neuroscience, 8, p.2640–2651, 1988].

However, the relationship of this restricted cleavage of α-fodrin to Sjögren's syndrome remains to be known.

Therefore, if an autoantibody or autoantigen specific to Sjögren's syndrome, particularly primary Sjögren's syndrome, is discovered, not only will the diagnosis of Sjögren's syndrome be faciliated and made more definite but the prophylaxis and therapy of Sjögren's syndrome, particularly primary Sjögren's syndrome, and, hence, prevention of progression of primary to secondary syndrome will be made possible by establishing a tolerance to autoantigens prior to onset of the disease or after the onset.

Furthermore, detailed analyses for elucidation of the mechanisms of onset of Sjögren's syndrome will also become feasible.

SUMMARY OF THE INVENTION

In view of the above state of the art, the inventors of the present invention did much research and not only discovered autoantibodies which are specifically detected in primary Sjögren's syndrome but also found that the corresponding autoantigens are α-fodrin and α-fodrin fragment proteins.

The inventors further found that Sjögren's syndrome can be prevented and cured by administering such an autoantigen.

The present invention, therefore, is directed to:

(1) A pharmaceutical composition comprising α-fodrin, a mutein thereof, a fragment thereof, or a salt thereof with a pharmaceutically acceptable carrier, (2) A composition for preventing or treating autoimmune disease comprising α-fodrin, a mutein thereof, a fragment thereof, or a salt thereof with a pharmaceutically acceptable carrier, (3) A composition for preventing or treating Sjögren's syndrome comprising α-fodrin, a mutein thereof, a fragment thereof, or a salt thereof with a pharmaceutically acceptable carrier, (4) The composition described in the above item (3) wherein the molecular weight of said α-fodrin, a mutein thereof, or a fragment thereof is from about 2 K to about 240 K, (5) The composition described in the above item (3) wherein said α-fodrin, a mutein thereof, or a fragment thereof contains or comprises an amino acid sequence substantially shown by Arg-Gln-Lys-Leu-Glu-Asp-Ser-Tyr-Arg-Phe-Gln-Phe-Phe-Gln-Arg-Asp-Ala-Glu-Glu-Leu SEQ ID NO: 1, (6) The composition described in the above item (5) wherein the molecular weight of said α-fodrin, a mutein thereof, or a fragment thereof is from about 100 K to about 140 K, (7) The composition described in the above item (3) wherein said α-fodrin fragment is an α-fodrin fragment protein available upon proteolysis of α-fodrin with a protease, (8) A diagnostic agent for autoimmune disease comprising α-fodrin, a mutein thereof, a fragment thereof, or a salt thereof, (9) A diagnostic agent for Sjögren's syndrome comprising α-fodrin, a mutein thereof, a fragment thereof, or a salt thereof, (10) The diagnostic agent for Sjögren's syndrome described in the above item (9) wherein the molecular weight of α-fodrin, a mutein thereof, or a fragment thereof is from about 2 K to about 240 K, (11) The diagnostic agent for Sjögren's syndrome described in the above item (9) wherein said α-fodrin, a mutein thereof, or a fragment thereof contains or comprises an amino acid sequence substantially shown by Arg-Gln-Lys-Leu-Glu-Asp-Ser-Tyr-Arg-Phe-Gln-Phe-Phe-Gln-Arg-Asp-Ala-Glu-Glu-Leu SEQ ID NO:1, (12) The diagnostic agent for Sjögren's syndrome described in the above item (11) wherein the molecular weight of α-fodrin, a mutein thereof, or a fragment thereof is from about 100 K to about 140 K, (13) A method for detection or assay of an antibody against α-fodrin, a mutein thereof, a fragment thereof, or a salt thereof, which comprises contacting α-fodrin, a mutein thereof, a fragment thereof, or a salt thereof with said antibody.

(14) A method for preventing or treating autoimmune disease which comprises administering to a patient a therapeutically effective amount of α-fodrin, a mutein thereof, a fragment thereof, or a salt thereof with a pharmaceutically acceptable carrier, (15) The method described in the above item (14), wherein autoimmune disease is Sjögren's syndrome, (16) A method for diagnosing autoimmune disease which comprises detecting or assaying autoantibody against α-fodrin, a mutein thereof, a fragment thereof, or a salt thereof, which comprises contacting α-fodrin, a mutein thereof, a fragment thereof, or a salt thereof with said autoantibody, (17) The method described in the above item (16), wherein autoimmune disease is Sjögren's syndrome, (18) Use of α-fodrin, a mutein thereof, a fragment thereof, or a salt thereof for the manufacture of a medicament for preventing or treating autoimmune disease, (19) Use of α-fodrin, a mutein thereof, a fragment thereof, or a salt thereof for the manufacture of a medicament for preventing or treating Sjögren's syndrome, (20) Use of α-fodrin, a mutein thereof, a fragment thereof, or a salt thereof for the manufacture of a medicament for diagnosing autoimmune disease, or (21) Use of α-fodrin, a mutein thereof, a fragment thereof, or a salt thereof for the manufacture of a medicament for diagnosing Sjögren's syndrome.

BRIEF DESCRIPTION OF THE DRAWINGS

FIGS. 6A & B shows western blots of the fusion protein (A) and α-fodrin fragment protein (B) obtained in Example 2 using the serum from a mouse with Sjögren's syndrome 6A (Disease) or the serum from a mouse without the syndrome 6B (Normal).

FIGS. 8A & B show electrophoregram (FIG. 8A) showing the calpain cleavage of murine α-fodrin protein as investigated using intact murine α-fodrin protein (α-fodrin) and murine calpain-treated α-fodrin protein (calpain treated) and the corresponding Western blots (FIG. 8B) using the serum from a mouse with Sjögren's syndrome.

DETAILED DESCRIPTION OF THE INVENTION

α-Fodrin or a mutein thereof, a fragment thereof, or a salt thereof, which can be used in the present invention, includes but is not limited to human α-fodrin proteins, and there is no limitation on biological species or molecular weight provided that it is immunochemically equivalent to human α-fodrin protein itself or any fragment protein available on restricted cleavage of said α-fodrin protein by a protease or proteases.

The term "immunochemically equivalent" is used herein to mean the state of being biologically indistinguishable in antibody reactivity and antigenicity and, to cite a specific example, being recognizable by the same antibody or antiserum.

The above-mentioned α-fodrin, mutein, fragment protein, and salt may be those purified from organisms or those obtained by recombinant biotechnology. Particularly when they are produced by genetic engineering technology, there may be mutations, substitutions, insertions, additions or deletions of amino acids unless the immunochemical equivalence is lost. Moreover, side chains of the constituent amino acids of these proteins may be protected by suitable protective groups [e.g. $C_{1-6}$ acyl groups such as formyl, acetyl, etc. (preferably $C_{1-6}$ alkanoyl)] unless said immunochemical equivalence is lost.

To be more specific, the α-fodrin fragment protein that can be used in the present invention includes proteins available upon cleavage of human α-fodrin with proteases and is preferably one containing a partial sequence of human α-fodrin, particularly the amino acid sequence of SEQ ID NO:1 or an amino acid sequence immunochemically equivalent thereto.

The protease that can be used with advantage includes trypsin, chymotrypsin, and calpain (preferably calpain).

In addition to the above proteins, α-fodrins derived from any tissues (e.g. brain) or cells of warm-blood animals (e.g. guinea pig, rat, mouse, rabbit, swine, sheep, cattle, monkey, etc.) or the proteins available upon proteolysis of the α-fodrins with said proteases. Preferred are proteins containing the amino acid sequence of human α-fodrin shown by SEQ ID NO:1 or an amino acid sequence immunochemically equivalent thereto and being immunochemically equivalent as the whole. The cleavage of α-fodrin protein with a protease can be achieved by allowing them to react in a buffer solution of pH from about 6 to about 8 at from about 10 to about 50° C. (preferably from about 30 to about 45° C.) for from about 30 minutes to about 5 hours.

Therefore, although the quantitative and qualitative factors such as amino acid composition of α-fodrin or its fragment protein may be diverse, its molecular weight is preferably from about 2 K to about 240 K and, for still better results, from about 100 K to about 140 K. Particularly preferred is one showing a molecular weight of 120 K as determined by SDS-polyacrylamide gel electrophoresis.

The salt of α-fodrin and of an α-fodrin fragment protein in the context of the present invention may be any kind of salt but is preferably an acid addition salt and, in particular, a physiologically acceptable acid addition salt.

The preferred examples of such salt are salts with inorganic acids (e.g. hydrochloric acid, phosphoric acid, hydrobromic acid, sulfuric acid, etc.) or salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.).

The mutein of α-fodrin protein in the context of the present invention is a protein available upon mutation, substitution, insertion, addition and/or deletion of amino acids of α-fodrin protein barring loss of immunochemical equivalence.

The mutein more specifically includes a variety of proteins available upon mutation of the amino acid sequence of the parent protein, for example those available-upon addition of amino acids, deletion of constituent amino acids, or substitution of different amino acids for constituent amino acids.

The addition of amino acids includes addition of at least one amino acid (preferably at most 5 amino acids).

The deletion of constituent amino acids includes deletion of at least one amino acid (preferably at most 5 amino acids) constituting α-fodrin.

The substitution of other amino acids includes substitution of at least one amino acid (preferably at most 5 amino acids) of α-fodrin.

The number of added amino acids is at least one but not limited unless the characteristics of α-fodrin, particularly immunological equivalence to the intact α-fodrin protein, are lost.

The number of constituent amino acids deleted in the deletion mutein of α-fodrin is at least one but there is no limitation on the number of deletions unless the characteristics of α-fodrin, particularly the immunological equivalence to α-fodrin protein, are lost.

The number of constituent amino acids of α-fodrin substituted in the substitution mutein is at least one but not limited unless the characteristics of α-fodrin, particularly immunological equivalence to the intact α-fodrin protein, are lost.

The constituent amino acids replaced in the substitution mutein may be cysteine and/or other amino acids but preferably cysteine is replaced. The amino acids other than cysteine that may be replaced are aspartic acid, arginine, glycine, and valine, among others.

When the constituent amino acid replaced is cysteine, the substitute amino acid is preferably a neutral amino acid, for instance. The neutral amino acid that-can be used includes but is not limited to glycine, valine, alanine, leucine, isoleucine, thyrosine, phenylalanine, histidine, tryptophan, serine, threonine, and methionine. Particularly preferred are serine and threonine.

Where the constituent amino acid to be replaced is an amino acid other than cysteine, the substitute amino acid is selected from among those amino acids which are different from the amino acid to be replaced in hydrophilicity or hydrophobicity, or in electric charge. Specifically, when the amino acid to be replaced is aspartic acid, for instance, the substitute amino acid may for example be asparagine, thereonine, valine, phenylalanine, or arginine, but asparagine or arginine is particularly preferred.

When the amino acid to be replaced is arginine, the substitute amino acid may for example be glutamine, threonine, leucine, phenylalanine, or aspartic acid, although glutamine is particularly preferred.

When the amino acid to be replaced is glycine, the substitute amino acid may for example be threonine, leucine, phenylalanine, serine, glutamic acid, or arginine, but threonine is particularly preferred.

When the amino acid to be replaced is serine, the substitute amino acid may for example be methionine, alanine, leucine, cysteine, glutamine, arginine, or aspartic acid but methionine is particularly preferred.

When the amino acid to be replaced is valine, the substitute amino acid may for example be serine, leucine, proline, glycine, lysine, or aspartic acid, but serine is particularly preferred.

The preferred amino acids to be replaced are aspartic acid, arginine, glycine, serine, valine, etc. and the preferred substitute amino acids are asparagine, glutamine, arginine, threonine, methionine, serine, and leucine.

In the substitution mutein, two or more substitutions may be concurrently involved. It is particularly preferable that 2 or 3 amino acids be substituted.

The above mutein may represent a combination of any two or three of the addition, deletion, and substitution described above. For the production of such a mutein, the method for site-directed mutagenesis is employed. This well-known method is described in Lather, R. F. and Lecoq, J. P., Genetic Engineering, p.31–50, Academic Press, 1983. The oligonucleotide-directed mutagenesis technique is described in Smith, M. and Gillam, S., Genetic Engineering, Principles and Methods, Vol. 3, p.1–32, Prenam Press, 1981.

The structural gene coding for the mutein can be produced typically by the following procedure.

(a) Hybridize a single-stranded DNA comprising the single-stranded DNA chain of the structural gene of α-fodrin with a mutagenic oligonucleotide primer (this primer must be complementary to the cysteine codon to be replaced or, depending on cases, a domain including the antisense triplet pairing with said codon. However, mismatch with other amino acid encoding codons or, depending on cases, the antisense triplet is acceptable).

(b) Extend the primer with DNA polymerase to produce a mutagenic heteroduplex.

(c) Replicate this mutagenic heteroduplex.

Then, the phage DNA transporting the mutated gene is isolated and introduced into a plasmid.

The plasmid thus obtained is used to transform a suitable host and the resulting transformant is grown in a medium so as to produce the desired mutein.

While the α-fodrin, α-fodrin fragment thereof, or a salt thereof can be produced in accordance with the methodology described above, they can also be produced by culturing a transformant containing a DNA fragment encoding the full-length α-fodrin or α-fodrin fragment protein as described hereinafter.

Furthermore, they may also be produced by the method for peptide synthesis as described hereinafter.

The DNA sequence coding for the complete sequence of human α-fodrin protein for use in the present invention is disclosed in Journal of Biological Chemistry, 265, p.4427–4433, 1990. Therefore, for the production of said α-fodrin or α-fodrin fragment protein, the DNA fragment can be obtained and either the whole or a portion be conveniently used.

The full length or part of the DNA can be cloned from the genomic DNA of a warm-blood animal (e.g. man etc.), the genome DNA library of a warm-blooded animal (e.g. man etc.), the cDNA of a warm-blooded animal (e.g. man etc.) tissue or cell, or the cDNA library of a warm-blooded animal (e.g. man etc.) tissue or cell by the following procedure.

The vector for the library may be a bacteriophage, plasmid, cosmide, or phagimide.

Moreover, an mRNA fraction obtained form a tissue or cell can be amplified by the known reverse transcriptase-polymerase chain reaction technique (RT-PCR method).

Furthermore, partial base sequences may respectively be chemically synthesized and condensed together.

The detailed procedures are as follows.

As regards the method for cloning the full length or a fragment of the DNA coding for α-fodrin and α-fodrin fragment protein for use in the present invention, the necessary amplication can be achieved by the known polymerase chain reaction method (PCR method) using synthetic DNA primers having a partial base sequence of α-fodrin fragment protein or screened by hybridization of a DNA fragment inserted in a suitable vector to-a DNA fragment coding for α-fodrin or α-fodrin fragment protein or a synthetic DNA-conjugate thereof. The hybridization can be carried out typically by the method described in Molecular Cloning, 2nd ed. (J. Sambrook et. al., Cold Spring Harbor Lab. Press, 1989). When a commercial library is used, the procedure described in the accompanying manual can be followed.

The cloned DNA fragment coding for α-fodrin and α-fodrin fragment protein can be used either as it is or, if desired, after digestion with a restriction enzyme or after addition of a linker. This DNA fragment may have TAG as the translation initiation codon at its 5'-end and TAA, TGA, or TAG as the translation termination codon at its 3'-end. The translation initiation codon and traslation termination codon can also be added through suitable synthetic DNA adapters.

The expression vector for α-fodrin and α-fodrin fragment protein can be produced by, for example,
  (a) cloning the objective DNA fragment from the DNA encoding the α-fodrin or α-fodrin fragment protein of this invention and
  (b) ligating this DNA fragment downstream of the promoter in a suitable expression vector.

The vector that can be used includes plasmids of the *E. coli* origin (e.g. pBR322, pBR325, pUC12, pUC13, etc.), plasmids of the *B. subtilis* origin (e.g. pUB110, pTP5, PC194, etc.), plasmids of the yeast origin (e.g. pSH19, pSH15, etc.), λ phage and other bacteriophages, and animal viruses such as retrovirus, vaccinia virus, baculovirus, etc.

The promoter that can be used in the present invention can be any suitable promoter for the host used in gene expression.

When the host to be transfected is a microorganism of the genus Escherichia, trp promoter, lac promoter, recA promoter, λPL promoter, lpp promoter, etc. can be used. When the host is a microorganism of the genus Bacillus, SP01 promoter, SP02 promoter, penP promoter, etc. can be employed. When the host is a yeast, PH05 promoter, PGK promoter, GAP promoter, ADH promoter, etc. can be used with advantage.

When the host is an animal cell, SV40-derived promoter, retrovirus promoter, metallothionein promoter, heat shock promoter, cytomegarovirus promoter, and SRα promoter, among others, can be employed.

In this connection, it is rewarding to use any of such promoters in conjunction with an enhancer compatible with the particular promoter.

When the host is a microorganism of the genus Escherichia, the alkaline phosphatase-signal sequence or OmpA-signal sequence, for instance, can be employed.

When the host is a microorganism of the genus Bacillus, the α-amylase-signal sequence, subtilisin-signal sequence, or the like can be used. When the host is a yeast, the mating factor α-signal sequence, invertase-signal sequence, or the like can be used. When the host is an animal cell, the insulin-signal sequence, α-interferon-signal sequence, antibody molecule-signal sequence, etc. can be utilized.

Where necessary, a signal sequence suited to the host can be added to the 5'-end of the DNA fragment coding for the α-fodrin or α-fodrin fragment protein.

Moreover, where necessary, the sequence of a marker protein such as glutathione S-transferase or the like may be added to either the 5'-end or the 3'-end of the DNA fragment encoding α-fodrin or an α-fodrin fragment protein. This marker sequence is useful for the purification of α-fodrin protein [Gene, 67, p.31, 1988]. Moreover, the marker protein can be separated from α-fodrin or α-fodrin fragment protein by, for example, cleavage with a protease after optional purification [Gene, 67, p.31, 1988].

Using a vector containing the thus-constructed DNA fragment coding for α-fodrin or α-fodrin fragment protein, a transformant can be produced. As the host, a microorganism of the genus Escherichia or of the genus Bacillus, a yeast, an insect, or an animal cell can be employed.

The microorganism of the genus Escherichia that can be employed includes *Escherichia coli* K12·DH1 [Proc. Natl. Acad. Sci. U.S.A, 60, p.160, 1968], JM103 [Nucleic Acids Research, 9, p.309, 1981], JA221 [Journal of Molecular Biology, 120, p.517, 1978], HB101 [Journal of Molecular Biology, 41, p.459, 1969], and C600 [Genetics, 39, p.440, 1954], among other strains.

The microorganism of the genus Bacillus that can be employed includes *Bacillus subtilis* ML114 [Gene, 24, p.255, 1983] and 207–21 [Journal of Biochemistry, 95, p.87, 1984], among others.

The yeast that can be used includes *Saccharomyces cerevisiae* AH22, AH22R⁻, A87-11A, DXD-5D, and 20B-12, among others.

The insect that can be used includes silkworm larva [Maeda et al., Nature, 315, p.592, 1985].

The animal cell that can be used includes but is not limited to monkey cell line COS-7, Vero cell line, Chinese hamster cell line CHO, DHFR gene-defected Chinese hamster cell line CHO (dhfr⁻CHO cell line), mouse L cell, mouse myeloma cell, and human FL cell line, among other cells.

Transfection of a microorganism of the genus Escherichia can be carried out typically by the methods described in Proc. Natl. Acad. Sci. USA, 69, p.2110 (1972) and Gene, 17, p.107 (1982).

Transfection of a microorganism of the genus Bacillus can be carried out typically by the methods described in Molecular & General Genetics, 168, p.111 (1979) and other literature.

Transfection of a yeast can be carried out typically by the method described in Proc, Natl, Acad, Sci, USA, 75, p.1929 (1978).

Transfection of an insect cell can be carried out typically by the method described in Bio/Technology, 6, p.47–55, (1988).

Transfection of an animal cell can be carried out typically by the method described in Virology, 52, p.456 (1973).

In this manner, a transformant produced by transfection with an expression vector containing a DNA fragment encoding α-fodrin or α-fodrin fragment protein can be obtained.

The culture medium that can be used for culture of a transformant obtained by using a microorganism of the genus Escherichia or Bacillus as the host is preferably a liquid medium containing sources of carbon and nitrogen, inorganic salts, and other components necessary for multiplication of the transformant.

The source of carbon that can be used includes glucose, dextrin, soluble starch, sucrose, etc. and the source of nitrogen includes varieties of inorganic or organic nitrogenous substances such as ammonium salts, nitrates, corn steep liquor, peptone, casein, meat extract, soybean cake, and potato extract. Among the inorganic salt that can be used are calcium chloride, sodium dihydrogen phosphate, and magnesium chloride, to mention just a few.

Further, yeast extract, vitamins, growth factors, etc. can also be added.

The pH of the medium is preferably from about 5 to about 8.

The preferred culture medium that can be used for culture of a microorganism of the genus Escherichia includes M19 medium supplemented with glucose and casamino acids [Miller, Journal of Experiments in Molecular Genetics, p.431–433, Cold Spring Harbor Laboratory, New York, 1972]. To this medium may be added a certain chemical, such as 3β-indolylacrylic acid, where necessary, so as to allow the promoter to function with improved efficiency.

When the host is a microorganism of the genus Escherichia, the transformant is usually cultured at from about 15 to about 43° C. for about from 3 to about 24 hours, with aeration and agitation where necessary.

When the host is a microorganism of the genus Bacillus, the transformant is usually cultured at from about 30 to about 40° C. for from about 6 to about 24 hours, with aeration and agitation where necessary.

The medium that can be used for culture of a transformant constructed using a yeast as the host includes but is not limited to Burkholder's Minimal Medium [Bostian, X. L. et. al., Proc. Natl. Acad. Sci USA, 77, p.4505 (1980)] and 0.5% casamino acids-supplemented SD Medium [Bitter, G. A. et al., Proc Natl. Acad. Sci. USA, 81, p.5330 (1984)]. The pH of the medium is preferably adjusted to form about 5 to about 8. The transformant is cultured usually at from about 20 to about 35° C. for from about 24 to about 72 hours, with aeration and agitation where necessary.

When the host is an insect cell, the culture medium that can be used for culture of the transformant includes Grace's Insect Medium (Grace, T. C. C., Nature, 195, p.788 (1962) supplemented with suitable additives such as inactivated 10% bovine serum is used. The pH of the medium is preferably adjusted to from about 6.2 to about 6.4. The transformant is usually cultured at about 27° C. for from about 3 to 5 days, with aeration and agitation where necessary.

For culture of the transformant constructed using an animal cell as the host, the culture medium that can be used includes but is not limited to MEM supplemented with from about 5 to about 20% fetal calf serum [Science, 122, p.501 (1952)), DMEM [Virology, 8, p.396 (1959)], RPMI1640 [The Journal of the American Medical Association, 199, p.519 (1967)], and 199 Medium [Proceeding of the Society for the Biological Medicine, 73, p.1 (1950)]. The pH of the medium is preferably from about 6 to about 8. The transformant is cultured generally at from about 30 to about 40° C. for from about 15 to about 60 hours, with aeration and agitation where necessary.

Separation and purification of α-fodrin or α-fodrin fragment protein from the resulting culture broth can be typically carried out as follows.

For extration of the α-fodrin or α-fodrin fragment protein from grown bacterial or other cells, the cells are harvested by the known procedure and suspended in a suitable buffer solution. The suspended cells are disrupted by, for example, sonication, lysozyme treatment and/or freeze-thaw treatment and centrifuged or filtered to provide a crude extract of α-fodrin or α-fodrin fragment protein. The above-mentioned buffer may contain a protein denaturating agent such as urea or guanidine hydrochloride and/or a surfactant such as Triton X-100 (the tradename of Sigma).

When α-fodrin or its fragment protein is secreted extracellularly, the grown bacterial and other cells are removed by a per se known procedure and the supernatant is harvested.

The α-fodrin or α-fodrin fragment protein in the culture supernatant or extract can be purified by using per se known fractional purification techniques in a suitable combination.

Among such known fractional purification techniques are techniques utilizing a solubility differential, such as salting-out and solvent precipitation, techniques utilizing mainly a differential in molecular weight, such as dialysis, ultrafiltration, gel permeation chromatography, and SDS-polyacrylamide gel electrophoresis, techniques utilizing a difference in electric charge, such as ion exchange chromatography, techniques depending on specific affinity, such as affinity chromatography, a technique utilizing a difference in hydrophobicity, such as reversed phase high performance liquid chromatography, and techniques utilizing a differential in isoelectric point, such as electrofocusing.

The method for chemical synthesis of α-fodrin or an α-fodrin fragment protein may be whichever of solid-phase synthesis and liquid-phase synthesis.

Thus, the objective peptide can be synthesized by condensing a peptide fragment or amino acid constituting the protein of the invention with the remainder of the sequence and, where the product has protective groups, removing the protective groups.

The condensation and deprotection mentioned above can be carried out by, for example, the methods described in the following literature (1)–(5).

(1) M. Bodanszky and M. A. Ondetti, Peptide Synthesis, Interscience Publishers, New York (1966).

(2) Schroeder and Luebke, The Peptide, Academic Press. New York (1965).

(3) Izumiya, N. et al., Peptide Gosei no Kiso to Jikken (Fundamentals and Experiments in Peptide Synthesis), Maruzen, Ltd. (1975).

(4) Yatori, H. and Sakakibara, S., Seikagaku Jikken Koza 1 (Biochemical Experiment Series 1), Tanpakushitu no Kagaku (Protein Chemistry), p.205 (1977).

(5) Yatori, H. (ed.), Zoku Iyakuhin no Kaihatsu (Drug Development, Continued), vol. 14, Peptide Synthesis, Hirokawa Shoten.

After completion of the reaction, the protein of the present invention can be purified and isolated by using such techniques as solvent extraction, distillation, column chromatography, liquid chromatography, recrystallization, etc. in a suitable combination.

When the protein synthesized by the above method is a free peptide, it can be converted to a suitable salt by the known procedure. When a salt is obtained, it can be converted to the free peptide by the known procedure.

Thus, when the product α-fodrin, mutein, or fragment protein is a free peptide, it can be converted to a salt by a per se known procedure or a suitable procedure analogous therewith and when the product is a salt, it can be converted to the free peptide by the per se known procedure or a suitable procedure analogous therewith.

It is also possible to modify or trim the α-fodrin or α-fodrin fragment protein obtained by recombinant technology by causing a suitable protein-modifying enzyme to act on it either before or after purification.

The protein-modifying enzyme that can be used includes but is not limited to trypsin, chymotrypsin, arginyl end peptidase, protein kinase, and glucosidase.

The α-fodrin, mutein, fragment protein, or salt according to the present invention can be used in the form of a medicinal composition as a prophylactic and therapeutic drug for autoimmune diseases such as systemic lupus erythematosus, rheumatism, Sjögren's syndrome, etc., particularly as a drug for the prevention and treatment of Sjögren's syndrome.

Specifically, by administering α-fodrin or a mutein thereof, a fragment protein thereof, or a salt thereof, inflammations associated with autoimmune diseases, particularly inflammations of the lacrimal and salivary glands in Sjögren's syndrome can be treated or prevented.

If desired, the α-fodrin, mutein, fragment protein, or salt of the invention can be administered in combination with other known immunosuppresants and/or antiinflammatory agents in a suitable regimen for the prevention and treatment of autoimmune diseases, particularly the prevention and treatment of Sjögren's syndrome.

For application as a medicine, the α-fodrin, mutein, fragment protein, or salt of the present invention can be administered either as it is in bulk form or in a dosage form containing it in combination with a pharmaceutically acceptable carrier, excipient or diluent (e.g. as an injection, tablets, capsules, a liquid, an ointment, or a suppository etc.) to warm-blooded animals (e.g. man etc.) safely by the oral or other route.

Injections can be prepared by using physiological saline or an aqueous solution of glucose or the like in the routine manner.

Tablets, capsules, and other dosage forms can also be manufactured by the established corresponding pharmaceutical procedures.

As a medicine, the α-fodrin, mutein, fragment protein, or salt of the present invention is administered to warm-blooded animals in the doses selected from the daily dose range of from about 1 ng to about 100 μg/kg, preferably from about 10 ng to about 10 μg/kg, taking the route of administration, clinical symptoms, and other factors into consideration.

The α-fodrin, mutein, fragment protein, or salt of the present invention can be used for the diagnosis of autoimmune diseases inclusive of Sjögren's syndrome.

Specifically, by detecting and assaying autoantibodies to the α-fodrin or α-fodrin fragment protein in the blood of a warm-blooded animal, the diagnosis, disease staging, or prediction of onset of autoimmune disease, particularly Sjögren's syndrome can be successfully accomplished.

The detection and assay of autoantibodies to α-fodrin and α-fodrin fragment protein can be made typically by the following method.

The α-fodrin, mutein, fragment protein, or salt (hereinafter referred to collectively as antigen protein) is coupled to a matrix such as cellulose beads in the routine manner. Then, the sample to be assayed is added and allowed to react at a given temperature (from about 4° C. to about 40° C.) for a given time.

After this reaction mixture is washed thoroughly, an antibody specifically binding to antibodies of the same species as that of the sample and labeled with a fluorescent substance, a chromogenic substance, an enzyme, or a radioisotope is added and allowed to react at a given temperature (from about 4° C. to about 40° C.) for a given time.

The reaction mixture is then washed thoroughly and, where necessary, a substrate for the enzyme is added and allowed to react at a given temperature (from about 4° C. to about 40° C.) for a given time. Then, the optical density, intensity of fluorescence, or scincillation count of the reaction product is determined.

The matrix that can be used for supporting the antigen protein in the above assay method includes gel beads [e.g. agarose gel (e.g. Sepharose 4B, Sepharose 6B (the trademark of Pharmacia Fine Chemicals (Sweden)) etc.), dextran gel (e.g Sephadex G-75, Sephadex G-100, Sephadex G-200 (the trademark of Pharmacia Fine Chemicals (Sweden)) etc.), polyacrylamide gel (e.g. Bio-Gel P-30, Bio-Gel P-60, Bio-Gel P-100 (the trademark of Bio-Rad Laboratories (U.S.A.)) etc.)], cellulose beads [e.g. Avicel (the trademark of Asahi Chemical Industry Co. Ltd.), ion exchange cellulose (e.g. diethylaminoethylcellulose, carboxymethylcellulose, etc.) etc.], physical adsorbents [e.g. glass (glass beads, glass rods, aminoalkyl glass beads, aminoalkyl glass rods, etc.), silicone flakes, styrenic resin (e.g. polystyrene beads, polystyrene particles, etc.), immunoassay plates (e.g. the product of Nunc (Denmark)) etc.], ion exchange resin [e.g. weakly acidic cation exchange resin (e.g. Amberlite IRC-5 (the trademark of Rohm & Haas Company (U.S.A.)), Zeo-Karb 226 (the trademark of Permutit (West Germany)), and weakly basic anion exchange resin (e.g. Amberlite IR-4B, Dowex 3 (the trademark of Dow Chemical (U.S.A.)) etc.) etc.], among others.

The antigen protein can be immobilized on the matrix by the conventional procedures. For example, the cyanogen bromide method and glutaraldehyde method described in Metabolism, 8, p.696 (1971) can be mentioned. As a more expedient procedure, the antigen protein can be physically adsorbed on the matrix.

The label for the antibody-label conjugate (labeled antibody) can for example be a radioisotope, an enzyme, a fluorescent substance, or a chromogen but the use of an enzyme is preferred.

The enzyme is preferably a stable enzyme with high specific activity, such as peroxidase, alkaline phosphatase, β-D-glactosidase, glucose oxidase, etc., although peroxidase is most preferred.

The peroxidase may be of any origin or type, thus including the species available from horseradish, pineapple, fig, sweet patato, kidney bean, and corn, among other sources. Particularly preferred is horseradish peroxidase (HRP) extracted from horseradish.

In conjugating the antibody with such a peroxidase, it is convenient to use a maleimidated peroxidase so as to utilize the thiol group of the antibody molecule Fab'. As a method for maleimidating a peroxidase, the maleimide group can be introduced via the amino group of the peroxidase. For this purpose, the N-succinimidyl derivative of a maleimidocarboxylic acid can be employed and N-(γ-maleimidobutyryloxy)-succinimide (sometimes referred to briefly as GMBS) is used with advantage.

Thus, a certain intervening group may exist between the maleimide group and the peroxidase. To cause GMBS to react with peroxidase, the two reactants are incubated in a buffer of pH from about 6 to about 8 at a temperature of from about 10 to about 50° C. for from about 10 minutes to about 24 hours. The buffer mentioned above may for example be 0.1 M phosphate buffer with a pH value of about 7.0.

The thus-maleimidated peroxidase can be purified by, for example, gel filtration chromatography.

The matrix that can be used for said gel filtration chromatography includes Sephadex G-25 [the trademark of Pharmacia Fine Chemicals (Sweden)] and Bio-Gel P-2 [the trademark of Bio-Rad Laboratories (U.S.A.)], among others. The reaction between antibody and maleimidated peroxidase can be carried out in a buffer at a temperature of from about 0° C. to about 40° C. for from about 1 to about 48 hours. The buffer may for example be 0.1 M phosphate buffer containing 5 mM sodium ethylenediaminetetraacetate (pH 6.0).

The peroxidase-labeled antibody thus obtained can be purified typically by gel filtration chromatography.

The support that can be used for said gel filtration chromatography includes Sephadex G-25 [the trademark of Pharmacia Fine Chemicals (Sweden)] and Bio-Gel P-2 [the trademark of Bio-Rad Laboratories (U.S.A.)], among others.

As an alternative, a thiol group may be introduced into peroxidase, which can then be reacted with the maleimidated antibody molecule.

Coupling of an enzyme other than peroxidase with the antibody can also be carried out in a similar manner and any of the glutaraldehyde method, periodic acid method, and water-soluble carbodiimide method, for instance, can be utilized.

The assay method according to the present invention is now described in detail, taking the use of peroxidase as the label as an example, although the label that can be used is not limited to peroxidase.

In a first place, (1) A sample to be assayed is added to the antigen protein immobilized on a matrix to conduct an antigen-antibody reaction. Then, the above-prepared conjugate of peroxidase with an antibody binding to the antibodies of the same species as that of the sample (enzyme-labeled antibody) is added and reacted.

(2) To the reaction product obtained in (1), a substrate for peroxidase is added and the optical density or intensity of fluorescence of the reaction product is measured to calculate the enzymatic activity of the reaction product.

(3) The above procedures (1) and (2) are followed using standard solutions of the anti-α-fodrin or α-fodrin fragment protein antibody occurring in the serum from a patient with Sjögren's syndrome beforehand to construct a standard curve correlating the amount of the anti-α-fodrin or α-fodrin fragment protein antibody with the optical density or intensity of fluorescence.

(4) Using the serum from a patient with Sjögren's syndrome or a risk for the syndrome, the above procedures (1) and (2) are repeated and the measured optical density or intensity of fluorescence are fitted to the above standard curve to find the amount of the patient's anti-α-fodrin or α-fodrin fragment protein antibody.

Similarly, the diagnosis of Sjögren's syndrome can be made in accordance with a pre-constructed correlogram between the amount of anti-α-fodrin or α-fodrin fragment protein antibody and the probability of onset of Sjögren's syndrome.

Where, in this specification and the accompanying drawings, any base, amino acid, etc. are designated by abbreviations, the abbreviations recommended by IUPAC-IUB Commission on Biochemical Nomenclature or those used commonly in the art are employed. Some examples are listed below. For any amino acid that may exist as optically active forms, the L-compound is meant unless otherwise indicated.

DNA : deoxyribonucleic acid
cDNA : complementary deoxyribonucleic acid
mRNA : messenger ribonucleic acid
SDS : sodium dodecyl sulfate
EDTA : ethylenediaminetetraacetic acid
DEAE : diethylaminoethyl
Arg : arginine
Gln : glutamine
Lys : lysine
Leu : leucine
Glu : glutamic acid
Asp : aspartic acid
Ser : serine
Tyr : tyrosine
Phe : phenylalanine
Ala : alanine The SEQ ID NO mentioned under the title of Sequence Listing in this specification represents the following sequence.

SEQ ID NO:1 represents the amino acid sequence from the N-terminus through the 20-position of the autoantigen protein of 120 K obtained from an NFS/sld mouse as shown in Example 1.

EXAMPLES

The following examples are intended to describe the present invention in further detail and should by no means be construed as defining the scope of the invention.

Example 1

Characterization of the Autoantibodies and Autoantigens in a Sjögren's Syndrome Model NFS/sld Mouse It is known that when thymectomized on day 3 after birth, NFS/sld mice develop Sjögren's syndrome in 4–20 weeks after operation. Moreover, the symptoms observed then are known to well reflect the manifestations of primary Sjögren's syndrome (Hayashi, Y. and Haji, N., Clinical Immunology, 27, p.488–492 (1995), Hayashi, Y., Japanese Journal of Clinics, 53, 10, p.2383–2388 (1995), or Hashima et al., Journal of Immunology, 153, p.2769 (1994)].

NFS/sld mice were thymectomized on day 3 after birth and the serum was harvested after 4 weeks and 12 weeks. Using this serum and the serum obtained from BALB/c mice without Sjögren's syndrome, the presence of specific autoantibodies to Sjögren's syndrome was investigated.

Figure 1:
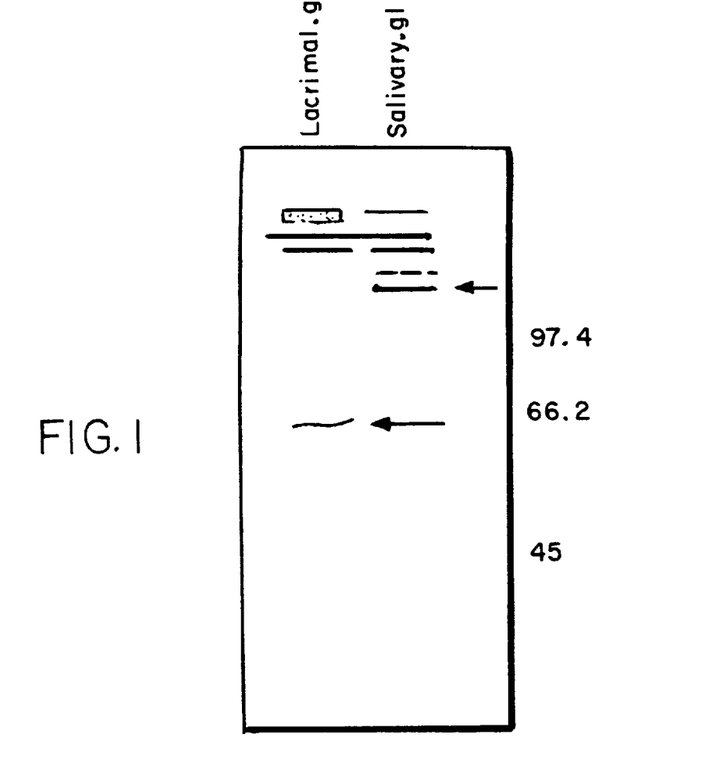
FIG. 1 shows electrophoregrams showing autoantigens in an NFS/sld mouse with Sjögren's syndrome as detected in its lacrimal gland (Lacrimal. gl) and salivary gland (Salivary. gl) extracts. In addition to autoantigens of 120 K and 60 K (indicated by arrowmarks), several other autoantigens, i.e. of 160 K, 240 K, etc., are observed.

Mouse salivary gland and lacrimal gland tissues were respectively homogenized in a Polytron homogenizer and suspended in 20 mM Tris-HCl (pH 7.2) containing 0.15 M sodium chloride, 5 mM benzamidine HCl, 2 mM diisopropyl fluorophosphate, 2 mM N-ethylmaleinimide, 2 mM phenylmethylsulfonyl fluoride, and 2 mM EDTA. The suspension was centrifuged at 20000×g for 30 minutes and the supernatant was subjected to SDS-polyacrylamide gel electrophoresis, transferred to a membrane filter, and reacted with the mouse serum. To this was added alkaline phosphatase-goat anti-mouse IgG antibody conjugate for a color reaction utilizing phosphatase activity. In this manner, autoantigens of 60 K, 120 K, 160 K, and 240 K were detected in the NFS/sld mouse salivary and lacrimal gland tissue homogenates (FIG. 1).

Figure 2:
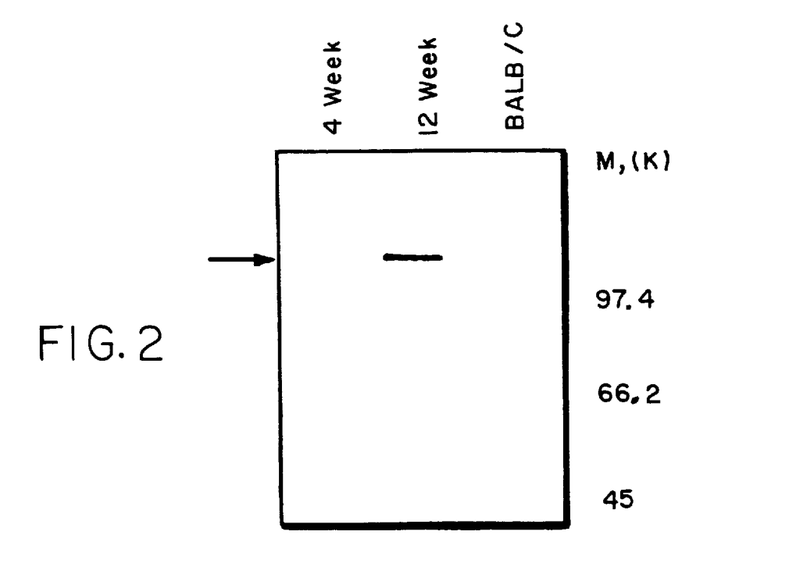
FIG. 2 shows electrophoregrams showing autoantigens in an athymic NFS/sld mouse at 4 and 12 weeks after operation at postnatal day 3. The legends "4 week", "12 week", and "BALB/c" indicate the serum from the athymic mouse after 4 weeks, the serum from the same mouse after 12 weeks, and the serum from a BALB/c mouse without Sjögren's syndrome, respectively.

At the same time, the presence of an autoantibodies recognizing the autoantigen of 120 K was detected in the serum from NFS/sld mice which developed Sjögren's syndrome 12 weeks after thymectomy (FIG. 2).

Figure 3:
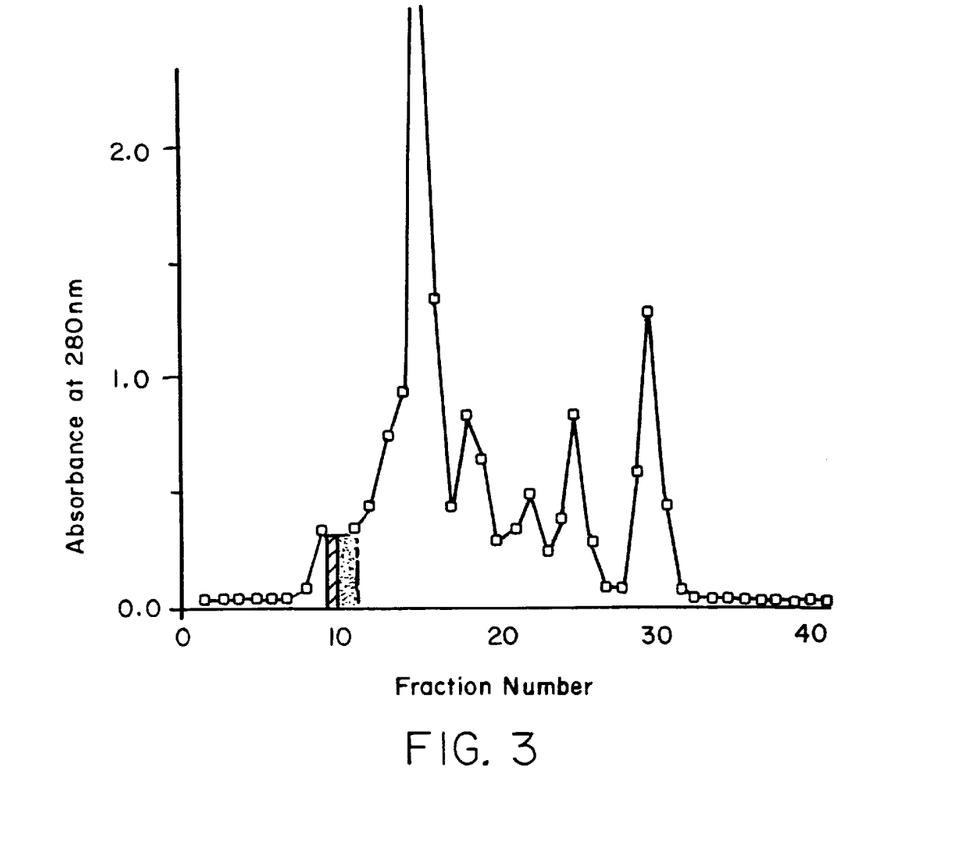
FIG. 3 shows gel filtration chromatogram of a murine salivary gland tissue homogenate. The recovered fraction is indicated by shading.
Figure 4:
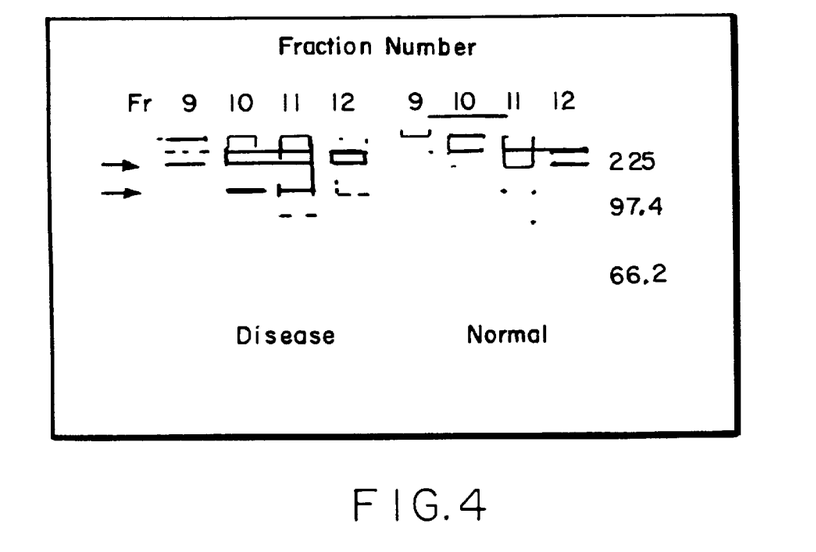
FIG. 4 shows western blots of the fraction recovered after gel filtration chromatography of the murine salivary gland tissue homogenate as indicated by shading (FIG. 3) as well as the preceding and subsequent fractions using the serum from a mouse with Sjögren's syndrome (Disease) or the serum from a mouse without Sjögren's syndrome (Normal).

Then, for characterization of the 120 K antigen protein reacting most intensely with the autoantibodies, the centrifugal supernatant of the mouse salivary gland homogenate was applied to Superose 12HR column (Pharmacia) for gel permeation chromatography using 20 mM Tris-HCl (pH 7.2) containing 1 M sodium chloride and 2 mM EDTA (FIG. 3). The fraction containing the 120 K molecule reacting with NFS/sld mouse antiserum was recovered and subjected to ion exchange chromatography (FIG. 4).

Figure 5:
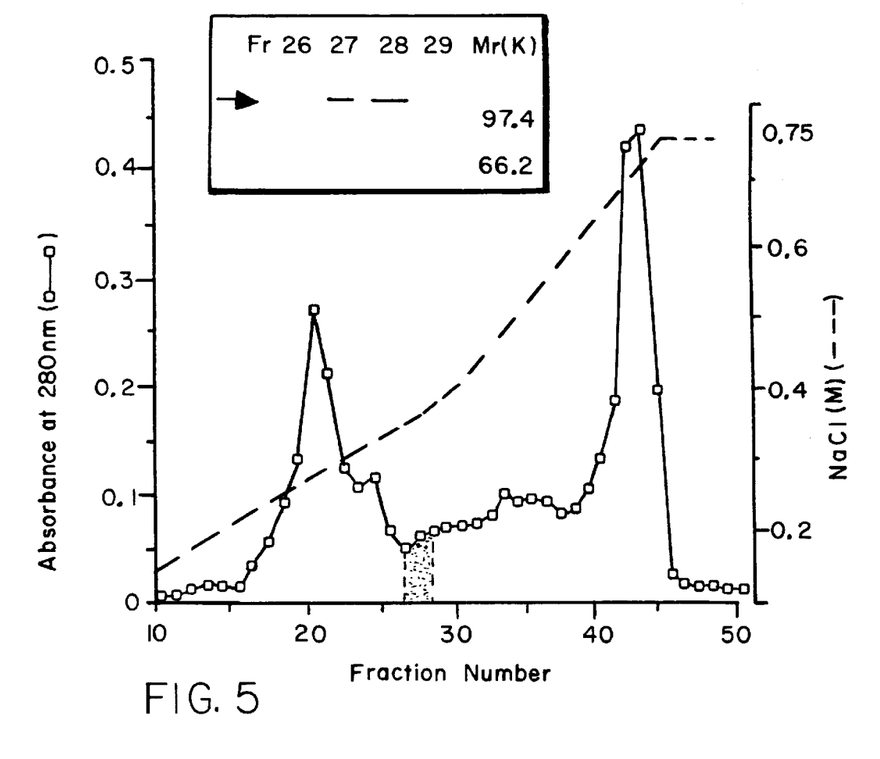
FIG. 5 shows ion-exchange chromatogram of the fraction recovered after gel filtration chromatography of the murine salivary gland tissue homogenate and the result of Western blotting using the recovered fraction (shaded area) and the serum from a mouse with Sjögren's syndrome.

The recovered fraction was dialyzed against 20 mM Tris-HCl (pH 7.2) containing 0.15 M sodium chloride and 2 mM EDTA and, then, applied to a DEAE-Cosmogel column (Nakarai Chemical). Elution was carried out on a gradient of 0.15 M–0.75 M sodium chloride (FIG. 5).

The fraction containing the 120 K molecule reacting with NFS/sld mouse antiserum was recovered, refractionated by 10% SDS-polyacrylamide electrophoresis, and transferred to a membrane filter. The clone corresponding to 120 K was isolated and analyzed for amino acid sequence using Applied Biosystems 477A protein sequencer. As a result, the amino acid sequence from the N-terminus through 20-position of the above 120 K autoantigen protein was in agreement with the known N-terminal sequence from 37-through 56-positions of human α-fodrin.

Example 2

Production of Human α-fodrin Fragment Protein

The DNA coding for human α-fodrin protein is known [Journal of Biological Chemistry, 265, p.4427–4433 (1990)].

A human α-fodrin fragment protein was produced using JS-1 containing a DNA fragment coding for the N-terminal region of the above DNA sequence.

The JS-1 DNA fragment (1–1784 bp) was completely digested with the restriction enzyme EcoRI and ligated to the EcoRI site of E. coli pGEK-2T vector (Pharmacia). According to the manufacturer's instructions for this vector, the vector was introduced into E. coli and the glutathione S-transferase-α-fodrin fragment protein fusion protein was harvested. According to the instructions, this fusion protein was digested with thrombin and the α-fodrin fragment protein was isolated and purified independently of glutathione S-transferase.

Figure 6:
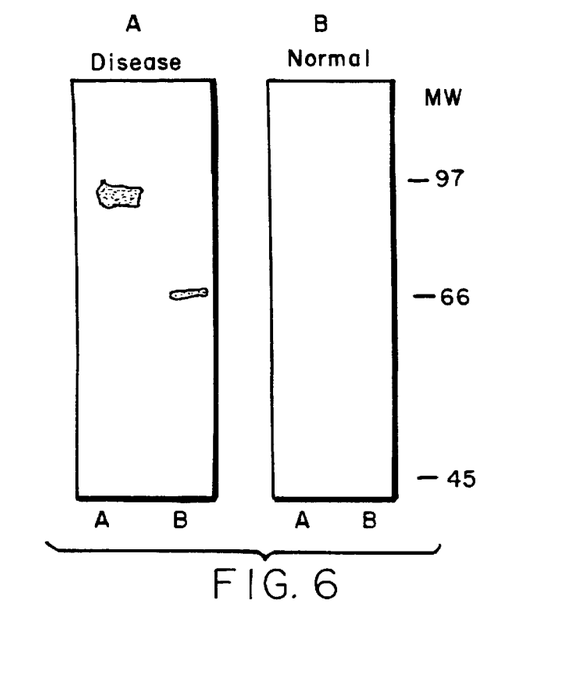

Using the above fusion protein and said α-fodrin fragment protein, their reactivity with sera from NFS/sld mice presenting with Sjögren's syndrome and NFS/sld mice not presenting with Sjögren's syndrome was investigated by Western blotting as in Example 1 (FIG. 6).

It was found that both the fusion protein and the α-fodrin fragment protein react with serum from the model mouse.

It was also found that since glutathione S-transferase does not react with sera from warm-blooded animals, the above fusion protein can be used without further processing for the purposes of the present invention.

Example 3

Figure 7:
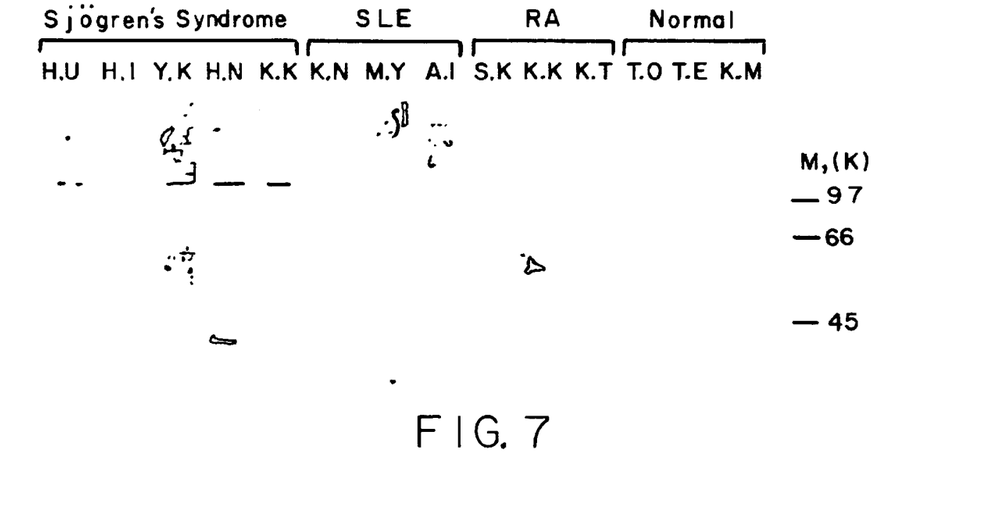
FIG. 7 shows electrophoregrams showing the results of screening for autoantibodies to the α-fodrin fragment protein by the Western blotting method using the fusion protein obtained in Example 2 and the sera from patients with Sjögren's syndrome (Sjögren's syndrome), sera from patients with systemic lupus erythematosus (SLE), sera from patients with chronic arthritis (RA), or sera from healthy subjects (Normal).

The Presence of α-fodrin Fragment Protein Autoantigens in Humans with Sjögren's Syndrome The fusion protein obtained in Example 2 was subjected to SDS-polyacrylamide gel electrophoresis and transferred to a filter membrane for immunoblotting. Then, using sera from patients with Sjögren's syndrome, sera from patients with systemic lupus erythematosus, sera from patients with chronic arthritis, or sera from healthy volunteers, autoantibodies to α-fodrin fragment protein were explored by the routine Western blotting technique (FIG. 7).

As a result, no autoantibody to the α-fodrin fragment protein was detected in the sera from patients with systemic lupus erythematosus or those with chronic arthritis. On the other hand, autoantibodies to the α-fodrin fragment protein of the present invention were found in sera from patients with Sjögren's syndrome.

It was, thus, clear that expression of autoantibodies to the α-fodrin fragment protein is specific to Sjögren's syndrome.

Example 4

The Inhibitory Effect of Human α-fodrin Fragment Protein on the Onset of Sjögren's Syndrome The inhibitory effect of the fusion protein obtained in Example 2 on the onset of Sjögren's syndrome was investigated.

Athymic NFS/sld mice, 3 weeks after operation at postnatal day 3, were intravenously dosed with a saline solution (25 μg/0.1 ml) of the fusion protein obtained in Example 2 or, as control, of either albumin-lysozyme or glutathione S-transferase. The animals were autopsied 8 weeks after administration and the severity of lesion was assessed by the method of White and Casarett using phathological indicators [Journal of Immunology, 112, p.178 (1974)]. The results are shown in Table 1.

In the group dosed with the α-fodrin fragment protein-glutathione S-transferase fusion protein, significant alleviations of lesions were found in all the submandibular gland, parotid gland and lacrimal gland tissues. In other organs, no phthalogical change was found.

TABLE 1

| Treatment | No. of mice examined | Grade of lesion (mean ± S.D) | | |
|---|---|---|---|---|
| | | Parotid gland | Submandibular gland | Lacrimal gland |
| Untreated | n = 6 | 2.52 ± 0.16* | 2.28 ± 0.18* | 2.17 ± 0.26* |
| α-fodrin | n = 7 | 0.28 ± 0.49* | 0.14 ± 0.38* | 0.28 ± 0.49* |
| Albumin | n = 5 | 2.55 ± 0.19 | 2.23 ± 0.14 | 2.01 ± 0.32 |
| Lysozyme | n = 5 | 2.48 ± 0.13 | 2.34 ± 0.18 | 2.18 ± 0.29 |
| Control | n = 5 | 2.58 ± 0.22 | 2.38 ± 0.28 | 2.22 ± 0.34 |

*: Significantly different at $p < 0.01$, Mann-Whitney's U test

Table 1 shows the relative efficacies for the symptomatic improvement of Sjögren's syndrome of no treatment (untreated), glutathione S-transferase-α-fodrin fragment protein fusion protein (α-fodrin), albumin, lysozyme, and glutathione S-transferase.

Example 5

Calpain-proteolysis of α-fodrin Protein

Figure 8:
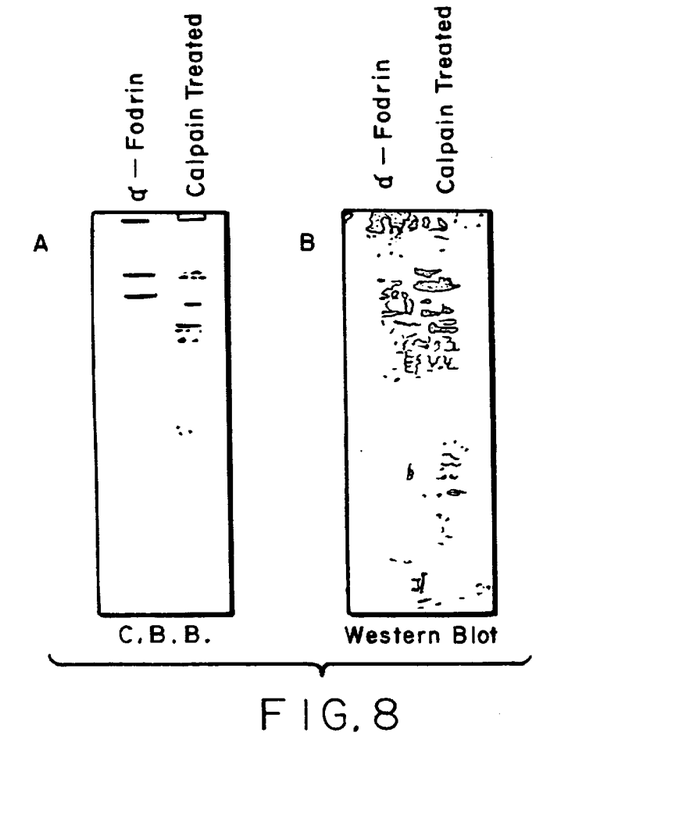

A mouse α-fodrin protein purified by the per se known method, 3 μg, was suspended in 50 mg imidazole hydrochloride (pH 7.2)-5 mM cysteine-1 mM calcium chloride and treated with 0.5 U of murine calpain (Sigma) at 37° C. for 60 minutes. The lysate was separated by SDS-polyacrylamide gel electrophoresis and Western blotted using antiserum from a mouse with Sjögren's syndrome (FIG. 8).

The antibodies to the α-fodrin or α-fodrin fragment protein of the present invention are detected in coincidence with the onset of Sjögren's syndrome which is an autoimmune disease. Therefore, the antigen protein of the present invention is of value as a diagnostic agent for autoimmune disease, particularly Sjögren's syndrome. Furthermore, since the antigen protein of the present invention remarkably inhibits the onset of illness when administered to a murine model of Sjögren's syndrome, it is apparent that the protein is of value as a prophylactic and therapeutic agent for autoimmune disease, particularly Sjögren's syndrome.

SEQUENCE TABLE

SEQ ID NO: 1
Length: 20
Type: amino acid
Topology: linear
Sequence type: peptide
Arg Gln Lys Leu Glu Asp Ser Tyr Arg Phe Gln Phe Phe Gln
    Arg Asp Ala Glu Glu Leu

What is claimed is:

1. A method for diagnosing Sjögren's syndrome which comprises detecting an autoantibody against α-fodrin, an antigenic fragment thereof, or a salt thereof, in a serum sample of a patient suspected of having an autoimmune disease which comprises contacting the serum sample with α-fodrin, an antigenic fragment thereof, or a salt thereof and detecting whether said autoantibody is present wherein the presence of said autoantibody is indicative of Sjögren's syndrome.

2. The method of claim 1, wherein the molecular weight of α-fodrin, or an antigenic fragment thereof is from about 2 kilodaltons to about 240 kilodaltons.

3. The method of claim 1, wherein said α-fodrin, or an antigenic fragment thereof comprises the amino acid sequence of SEQ ID NO: 1.

4. The method of claim 3, wherein the molecular weight of α-fodrin, or an antigenic fragment thereof is from about 100 kilodaltons to about 140 kilodaltons.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 20
      (B) TYPE: amino acid
      (C) TOPOLOGY: linear    (ii) MOLECULE TYPE: peptide    (iii) SEQUENCE DESCRIPTION: SEQ ID NO: 1:

```
Arg Gln Lys Leu Glu Asp Ser Tyr Arg Phe Gln Phe Phe Gln Arg
 1               5                  10                  15

Asp Ala Glu Glu Leu
                20
```